United States Patent [19]

Seltzer

[11] Patent Number: 5,834,656
[45] Date of Patent: Nov. 10, 1998

[54] SAMPLING INTERFACE FOR CONTINUOUS MONITORING OF EMISSIONS

[75] Inventor: Michael D. Seltzer, Ridgecrest, Calif.

[73] Assignee: The United States of America as represented by the Secretary of the Navy, Washington, D.C.

[21] Appl. No.: 932,233

[22] Filed: Sep. 17, 1997

[51] Int. Cl.$^6$ ...................................................... G01N 1/14
[52] U.S. Cl. ......................................................... 73/863.17
[58] Field of Search ............................ 73/863.01, 863.31, 73/863.83, 863.71–864.71; 356/316, 36

[56] References Cited

U.S. PATENT DOCUMENTS

| Re. 29,304 | 7/1977 | Greenfield et al. . | |
|---|---|---|---|
| 3,965,747 | 6/1976 | McCorckle . | |
| 3,965,748 | 6/1976 | Boubel et al. . | |
| 4,091,835 | 5/1978 | Frampton . | |
| 4,159,635 | 7/1979 | Sehmel . | |
| 4,272,483 | 6/1981 | Schick | 73/863.71 |
| 4,293,220 | 10/1981 | Denton et al. . | |
| 4,390,772 | 6/1983 | Hiratake . | |
| 4,470,316 | 9/1984 | Jiskoot | 73/863.31 |
| 4,482,246 | 11/1984 | Meyer et al. . | |
| 4,566,342 | 1/1986 | Kurz . | |
| 4,649,760 | 3/1987 | Wedding . | |
| 4,739,147 | 4/1988 | Meyer et al. . | |
| 4,823,622 | 4/1989 | Nohl et al. | 73/863.71 |
| 5,012,065 | 4/1991 | Rayson et al. . | |
| 5,090,257 | 2/1992 | Bruce . | |
| 5,479,254 | 12/1995 | Woskov . | |
| 5,526,110 | 6/1996 | Braymen . | |

OTHER PUBLICATIONS

J.D. Chase Theoretical and Experimental Investigation of Pressure and Flow in Induction Plasmas, journal of Applied Physics. nov. 1971 vol. 42, No. 12, pp. 4870–4879.

D. Truitt & J.W. Robinson Spectroscopic Studies of Organic Compunds Introduced into a Radio Frequency Induced Plasma. Analytica Chemica Acta, 51–1970 pp. 61–67 Elsevier Publishing Company, Amsterdam.

Seltzer, Michael D. An Argon ICP–Based Continous Emissions Monitor for Hazardous Air Pollutant Metals: Field Demonstration Presentation of the Ari Waste Management Association. 90th Annual Management Exhibition.

(List continued on next page.)

*Primary Examiner*—Robert Raevis
*Attorney, Agent, or Firm*—Melvin J. Sliwka; Stephen J. Church

[57] ABSTRACT

Sampling interfaces and methods of operation thereof having increased duty cycles and pressure equalizations that improve sensing of airborne metals in air samples fed to a continuous emissions monitor. Residual pressure in one or two sample reservoirs (loops) can be automatically equalized just prior to pneumatic connection between each sample reservoir loop and plasma in a plasma torch, thus minimizing or eliminating perturbation of the plasma. Deliberate sequential activation of valves allows each sample reservoir loop to be first isolated from the vacuum pump, and then momentarily as its pressure is equalized, it remains isolated from the plasma as well. Finally, pneumatic connection is made between each sample reservoir loop and the plasma allowing the contents of each sample reservoir (now at the same pressure as the plasma) to be transported into the plasma. Sampling interface having dual elongate sample reservoirs that alternate aliquots of sample air nearly doubles the rate of measurement of air entrained metals relative to a single elongate reservoir loop arrangement. By allowing measurements to be made at more frequent intervals using more representative sampling of extracted flue gases or air, the dual loops may permit the acquisition of hazardous emissions monitoring data that is more meaningful in terms of its temporal characteristics.

30 Claims, 6 Drawing Sheets

OTHER PUBLICATIONS

Seltzer, Michael D & Gerhard A. Meyer, Keeping and Eye on Metals Emissions, Environemntal Protection, Jun. 1997 vol. 8 No. 6—26–29.

Seltzer, Michael D. Continous Air Monitoring Using Inductively Coupled Plasma, Applied Spectorscopy, Submitted Jun. 1997.

Seltzer, Michael D. An Inductively Coupled Argon Plasma Continous Emissions Monitor forHazordous Air Pollutant Metals, Environmental Science and Technology Sept. 1997. submitted April 1997.

Emissions Measurement Branch, nsps Test Method, EMTIC M–002 Technical Support Division, QAQPS, EPA, NAWS China Lake.

SAMPLING INTERFACE FOR CONTINUOUS MONITORING OF EMISSIONS

STATEMENT OF GOVERNMENT INTEREST

The invention described herein may be manufactured and used by or for the Government of the United States of America for governmental purposes without the payment of any royalties thereon or therefor.

CROSS REFERENCE TO RELATED APPLICATIONS

This application is related to copending U.S. patent applications entitled "Modified Plasma Torch Design for Introducing Sample Air into Inductively Coupled Plasma" by Michael Seltzer in the U.S. Patent and Trademark Office application Ser. No. 08/932,397, filed Sep. 17, 1997 and "Correction of Spectral Interferences Arising from CN Emission in Continuous Air Monitoring Using Inductively Coupled Plasma Atomic Emission Spectrometry" by Michael Seltzer, U.S. Patent and Trademark Office application Ser. No. 08/932,023, filed Sep. 17, 1997 and "Method and Apparatus for Automated Isokinetic Sampling of Combustor Flue Gases for Continuous Monitoring of Hazardous Metal Emissions" by Michael Seltzer, U.S. Patent and Trademark Office application Ser. No. 08/932,401, filed Sep. 17, 1997 and incorporates all references and information thereof by reference herein.

BACKGROUND OF THE INVENTION

This invention relates to sampling interfaces for an emissions monitor. In particular, this invention relates to sampling interfaces and methods of operation thereof having increased duty cycles and pressure equalizations that improve sensing of airborne metals in air samples fed to a continuous emissions monitor.

Heretofore, the prior art in this field of invention involved measurement techniques that required batch sampling followed by chemical analyses of the collected samples at a later date. Because of the significant time delays between collection of samples and actual availability of analytical data, there was reduced confidence levels in the information provided by the prior art techniques. In addition, since most owners of hazardous waste combustors presently are required to demonstrate regulatory compliance on a yearly or bi-yearly basis, the unreliable techniques of the prior art have been found to be inadequate. In other words, the prior art did not offer a satisfactory way to measure continuous compliance.

A noteworthy advance in the state-of-the-art is disclosed in U.S. Pat. No. 5,596,405 that has provided a revolutionary new way to measure continuous compliance for toxic metal emissions. Hardware and methodology provide the capability for continuous, near-real-time monitoring of toxic metal emissions from hazardous waste combustors. The technology of this patent offers an unprecedented ability to obtain nearly instantaneous measurement of hazardous air pollutant metals from a stationary source, such as a waste incinerator or explosive ordnance deactivation furnace. Because of the repetitive nature of the measurements that this patented system provides, a high level of confidence in those measurements is assured.

U.S. Pat. No. 5,596,405 describes the use of a device called a sampling interface that contained a single sample reservoir or sample loop that was alternately filled with extracted sample air (while clean blank air was introduced into the plasma spectrometer) or purged using clean air, to pneumatically deliver an aliquot of sample air into a plasma spectrometer. During the purge and measurement portion of the cycle, extracted sample air was diverted directly to exhaust along with potentially valuable information. This sampling interface isokinetically extracted sample air from a smokestack at relatively high flow rates in accordance with regulatory dictates while permitting aliquots of the extracted air to be injected into the elemental analyzer (plasma torch and spectrometer) at constant low flow rates that are optimum for achieving good analytical results. The sampling interface is a key element in the successful operation of this technology and permits near-real-time continuous extraction of sample air and performs adequately. But, the sampling interface described in U.S. Pat. No. 5,596,405, as presently configured, has an inefficient duty factor for measurement. Measurement of sample air occurs for only a fraction of the time while the remaining time of each sampling cycle is spent waiting for the sampling reservoir or sampling loop in the sampling interface to be refreshed with extracted sample air or waiting for sample injection into the plasma to equilibrate before making measurements. In other words, because a considerable amount of time is spent waiting for sample collection and equilibration, the measurement process is intermittent and a considerable amount of potentially valuable information is lost during non-measurement periods. This may be particularly true in transient toxic metal emissions that may last for periods of time less than the lengths of present measurement cycles.

Another undesirable side effect of intermittent operation of the patented system is that periodic suctions are created as solenoids are switched. Sample air is extracted from the smokestack under vacuum by a vacuum pump located downstream of the sampling interface. This draws sample air through a long length of heated sample line required to transport sample air from smokestack to sampling interface, the length of the tubing used for the sample reservoir (loop), and the solenoid valves. At any given moment, a representative sample of air is resident in the sample reservoir and can be introduced into the plasma for measurement by activating the solenoid valves. But, because of the lengths of the lines and tubing, a residual vacuum is retained in the sample reservoir (loop) even after the solenoid valves are activated. When the solenoid valves are activated, the sample reservoir is completely isolated from the pump and its applied vacuum, and the sample reservoir (loop) is pneumatically connected instead at this point, to the plasma. Because gases and liquids naturally flow from a region of high pressure to one of low pressure, the residual vacuum left in the sample reservoir (loop) causes gases to be momentarily sucked out of the plasma, through the plasma torch, through the connecting tubing, and into the sample reservoir (loop).

The problem of unwanted residual vacuum in the system is exacerbated when high flow rates of flue gases are present during extraction of sample air from the flow. This is due to the direct relationship between pressure drop in a conduit and gas flow rate. It is, however, advantageous to extract the sample air from smokestacks emitting flue gases at relatively high flow rates (15–35 liters per minute) rather than at lower flow rates because the attendant high velocity of sample gases through the heated sample line facilitates efficient transport of entrained airborne particulate matter and helps minimize particulate losses due to settling.

The suction continues until the gas pressure inside the sample reservoir (residual vacuum) has equalized with the gas pressure in the plasma (atmospheric pressure) and the residual vacuum in the sample reservoir is relieved. Aside from the data being compromised, the two deleterious effects associated with this phenomenon involve: first, destabilization of the plasma for up several seconds that, under certain circumstances, will cause extinction of the plasma, and, second, thermal damage to the quartz torch caused by the sudden suction of hot plasma into the torch. In general, the effects of the residual vacuum are undesirable and worth any effort to mitigate or eliminate.

Thus, in accordance with this inventive concept, a need has been recognized in the state of the art for a sampling interface having pressure compensation and/or an increased duty cycle and that improve sensing of airborne materials by an emissions monitor.

SUMMARY OF THE INVENTION

The present invention is directed to providing a sampling interface that has first means coupled to an elongate reservoir for switching sample air flowing at a first rate and pressure into the elongate reservoir. Means are coupled to the elongate reservoir for coupling a first source of pressurized gas to it to change pressure therein from the first pressure to a second pressure. Second means are coupled to the elongate reservoir for switching a second source of pressurized gas thereto at the second pressure and a second flow rate different than the first flow rate to force the sample air in the elongate reservoir out of it at the second flow rate and pressure. The method for interfacing calls for switching sample air flowing at a first rate and pressure into an elongate reservoir. Then, coupling a first source of pressurized gas to the elongate reservoir changes pressure therein from the first pressure to a second pressure thereby preventing the transmission of suction force to plasma in a plasma torch. Switching a second source of pressurized gas to the elongate reservoir at the second pressure and a second flow rate different than the first flow rate forces the sample air in the elongate reservoir out of the elongate reservoir at the second flow rate and pressure.

An object of the invention is to provide an improved sampling interface.

Another object of the invention is to provide a sampling interface that avoids transmitting suctions that destabilize the plasma and may cause extinction of the plasma.

Another object of the invention is to provide a sampling interface that avoids transmitting suctions that cause thermal damage to the quartz torch resulting from sudden suction of plasma back into the torch.

Another object of the invention is to provide a sampling interface that automatically equalizes the residual pressure in the sample reservoir (loop) just before pneumatic connection between the sample reservoir (loop) and the plasma, thus minimizing or eliminating perturbation of the plasma.

Another object of the invention is to provide a sampling interface having an increased duty cycle.

Another object of the invention is to provide a sampling interface that improves the amount and reliability of the gathered data.

Another object of the invention is to provide a sampling interface incorporating a second sample reservoir or sample loop, so that wait times, normally required for a single sample reservoir to be recharged, are all but eliminated Another object of the invention is to provide a dual sample loop arrangement having reduced time to achieve steady state sample introduction into plasma from the present 15–20 second wait to an approximately 5-second wait since sample introduction will no longer alternate between sample air and clean air in a single loop.

These and other objects of the invention will become more readily apparent from the ensuing specification when taken in conjunction with the appended claims.

DESCRIPTION OF THE PREFERRED EMBODIMENTS

Figure 1:
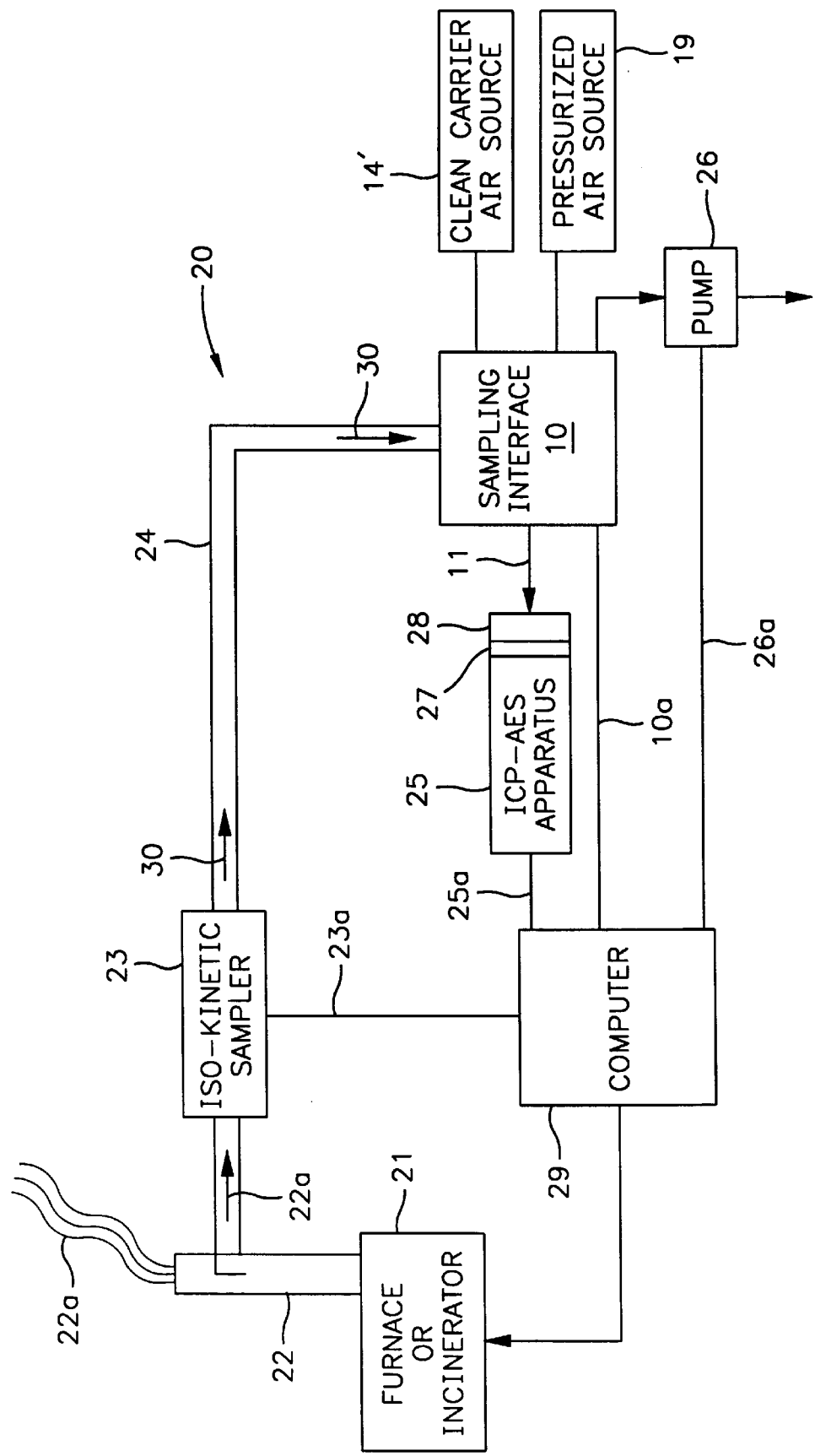
FIG. 1 is a schematic diagram of a system having a sampling interface according to this invention for collecting sample air and feeding it to a continuous emissions monitor.

In accordance with this invention FIG. 1 shows sampling interface 10 that is specifically designed for monitoring system 20 to interface sample air 30 with an analyzing apparatus 25. Apparatus 25 measures the concentration of entrained particulates in sample air 30, such as metals, and may rely on the technique known as inductively coupled plasma, atomic emission spectrometry (ICP-AES), see, for example, the above referred to U.S. Pat. No. 5,596,405.

Furnace or incinerator 21 has smokestack 22 ejecting flue gases 22a to the atmosphere. An automated isokinetic sampling system (isokinetic sampler) 23 provided with conventional sampling nozzle, flow sensors and regulated pump can be used to collect sample air 30 containing pollutant metals from incinerator 21 at the velocity flue gases 22a are emitted through smokestack 22. Isokinetic sampler 23 may be constructed using individual components (Please refer to NC 78564 Ser. No. 08/932,401 filed Sep. 17, 1997 for a more detailed explanation) or commercially available units may be selected, such as, for example, the isokinetic sampler model series 1275 marketed by Kurz Instruments of Monterey, Calif.

Sample air 30 is drawn through tubular sample line 24 and sampling interface 10 by vacuum pump 26. Sample line 24 is preferably heated and any suitable heating means can be used, such as a sample line, containing an electrical heating element that is marketed by Technical Heaters, Inc of San Fernando, Calif. Sample line 24 should be as short as possible to reduce the possibility of settling-out metal pollutants from sample air 30 as they travel from smokestack 22 to sampling interface 10.

ICP-AES apparatus 25 has plasma torch 27 with plasma 28 that receives sample air 30 from sampling interface 10 for analysis. For example, the plasma referred to could be an argon plasma at atmospheric pressure. Typical acceptable or optimum rates of introduction of sample air 30 into plasma 28 of ICP-AES apparatus 25 are between about 0.4 and 0.6 l/min., which also approximates the optimum carrier gas flow-rate during conventional operation of ICP-AES apparatus 25 during testing of liquid samples.

However, the acceptable, or optimum flow rates for introducing sample air 30 into plasma 28 is much lower than the flow rate used to extract sample air 30 from smokestack 22. Additionally, while the sample air extraction rate may vary considerably over time, the flow rate used for plasma introduction must remain absolutely constant to ensure precise and reproducible measurement, Sample air 30 is typically extracted at flow rates between 15–35 liters per minute. These high flow rates are required to achieve isokinetic extraction of airborne particulate matter containing the pollutant metals to be measured and to efficiently transport the particulate matter from the point of extraction to the analyzer, ICP-AES apparatus 25. Under isokinetic conditions, the velocity of extracted sample air 30 must exactly match the velocity of ejected flue gases 22a at the point of extraction. This ensures that particulate matter of different sizes and masses will be collected with equal efficiency and helps avoid particle size segregation during the extraction process. Moreover, isokinetic extraction ensures that a truly representative sample of air is collected by minimizing the effects of the different particle momenta that might otherwise contribute to particle size segregation and possible measurement bias, Naturally, as the velocity of ejected flue gas 22a varies over time, flow rate of the extracted sample air 30 must be varied accordingly to ensure that the velocity of extracted sample air 30 is exactly matched to the velocity of ejected flue gases 22a, The isokinetic sampling system is automated to sense changes in the velocity of ejected flue gases 22a and adjust the rate of sample air 30 extraction as needed. The flow rate of extracted sample air 30 is still far in excess of the optimum constant flow rate required for introduction into the plasma.

Therefore, before reaching plasma 28 of ICP-AES apparatus 25, sample air 30 is fed to sample interface 10. Sampling interface 10 accommodates the mismatch between relatively high sample flow-rates required for isokinetic sampling and collection of sample air 30 and the optimum flow-rates for required for introduction of sample air 30 into plasma 28. Sampling interface 30 also assures responsive operation of monitoring system 20 by blocking vacuum impulses that might interfere with plasma 28 of ICP-AES apparatus 25.

Computer 29 controls nearly all aspects of operation of the constituents of monitoring system 20. Control lines 23a extend between computer 29 and isokinetic sampler 23 to transmit appropriate control signals that initiate isokinetic sampling of flue gases 22a to create sample air 30. Computer control lines 23a extend between computer 29 and isokinetic sampler 23 to transmit appropriate control signals transmit appropriate control signals that initiate isokinetic sampling of flue gases 22a to create sample air 30. Computer control lines 26a extend between computer 29 and vacuum pump assembly 26 which contains the mass flow controller. The control signal regulates the mass flow controller which throttles the flow of sample air 30 drawn by the pump 26 through the sampling interface 10. Computer control lines 10a extend between computer 29 and sampling interface 10 to transmit appropriate control signals that activate its elements to draw in sampling air 30 at the higher velocities from conduit 24 and to feed sample air 30 to ICP-AES apparatus 25 through duct 11. Computer control lines 25a extend between computer 29 and ICP-AES apparatus 25 to transmit appropriate control signals that set up and execute the analysis process for the measurement of metals and other matter of interest in sample air 30 received from sampling interface 10. Computer control lines 21a extend between computer 29 and furnace 21 to transmit appropriate control signals that adjust or turn-off the furnace if certain emissions are found in the analysis of sample air 30 in ICP-AES apparatus 25 to exceed predetermined limits.

The appropriate computer control and synchronization signals for the aforedescribed elements of monitoring system 20 are generated in computer 29 in accordance with appropriate software and programming by one of ordinary skill in the art. Having the teachings of this invention in hand, one skilled in the art to which this invention pertains can suitably program a number of different computers and microprocessors available in the art to perform the required functions, including, but not limited to, generating appropriate computer control and synchronization signals, acquiring atomic emission data, converting analog to digital signals, initiating other monitoring, data acquisition, data storage, and termination of data acquisition, and coordinating control of the elements of monitoring system 20. Different monitoring conditions and operational parameters will call for different control signals and modified sequences of operation that can be accommodated within the scope of this invention. For example, different emissions or flue gas velocities might necessitate changed analysis procedures in ICP-AES 25, or that a different analysis device be used instead to acquire meaningful data. Such changes are within the scope of this invention.

Figure 2:
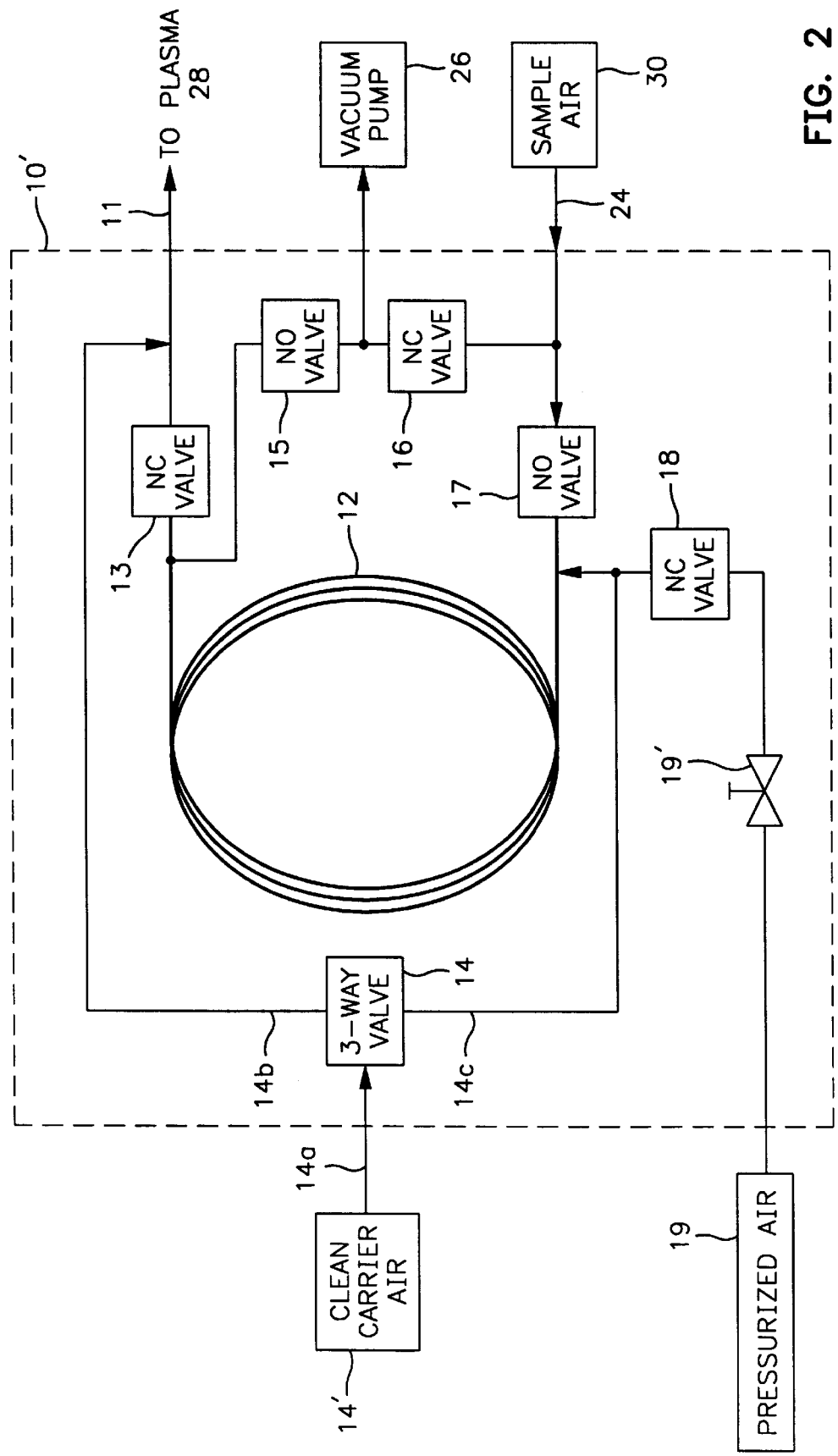
FIG. 2 is an embodiment of this invention that avoids the problems associated with vacuum in the sampling reservoir.

FIG. 2 illustrates one embodiment of an improved sampling interface 10' having a single sample reservoir 12 that may be an elongate length of tubing arranged in a loop. Typically, the tubing may be about thirty feet in length and could have one-half inch outer diameter and 0.41 inch inner diameter. Other lengths and sizes may be selected as well as a situation calls for. Residual pressure in sample reservoir 12 can be automatically equalized just prior to pneumatic connection between sample reservoir 12 and plasma 28, thus minimizing or eliminating perturbation of plasma 28. Solenoid activated valves 13, 14, 15, 16, 17, and 18 are activated in a deliberate sequential manner by appropriate control signals from computer 29. This sequential activation allows sample reservoir 12 to be, first, isolated from vacuum pump 26, then, for a moment as the pressure in sample reservoir 12 is equalized, sample reservoir 12 remains isolated from plasma 28 as well, and finally, pneumatic connection is made between sample reservoir 12 and plasma 28. This sequence delivers the contents of sample reservoir 12 (which is now at the same pressure as plasma 28) to plasma 28.

Sampling interface 10' primarily differs from the interface of U.S. Pat. No. 5,596,405 by inclusion of the feature that prevents vacuum pressures from being coupled to the plasma. Solenoid activated valves 13, 16, and 18 are marked as NC since they are normally closed and solenoid activated valves 15 and 17 are marked as NO since they are normally open. When activated, normally closed valves will open and normally open valves will close. Three-way solenoid activated valve 14 has one common input 14a connected to clean carrier air 14' at atmospheric pressure and two complementary output ports 14b and 14c. When three-way valve 14 is activated by control signals from computer 29, gas flow of clean air at 0.43 l/min. is diverted away from outlet port 14c associated with its unactivated state and exits through complementary outlet port 14b.

Heretofore, it was when the sampling interface of the above referred to patent switched between filling and purging that the most serious perturbation of plasma occurred. This perturbation has been reduced by the invention to inconsequential levels.

Figure 3A:
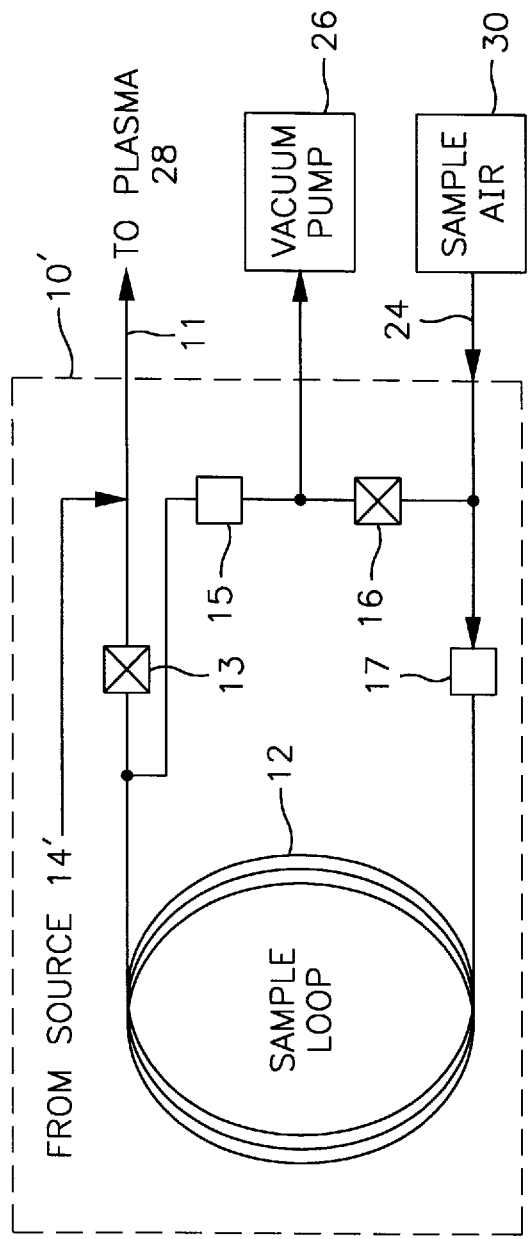
FIGS. 3A, 3B and 3C depict operational sequences of the embodiment of FIG. 2 that assure improved analyses.
Figure 3B:
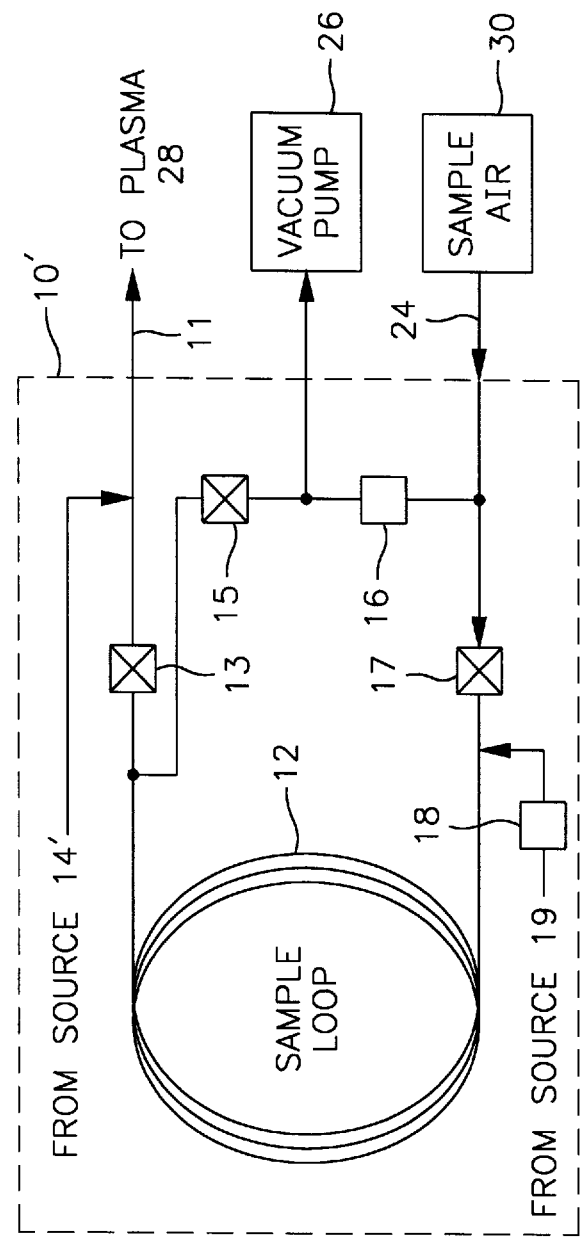
Figure 3C:
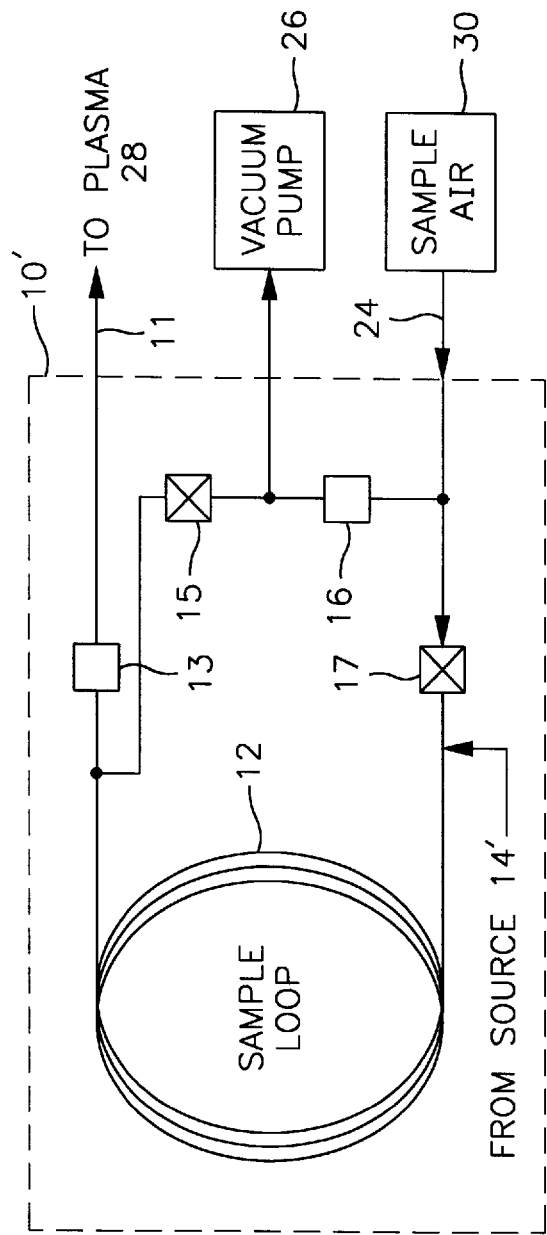

FIGS. 3A, 3B, and 3C show how sampling interface 10' operates and respectively depict only the valves and other elements that function in the associated description. FIG. 3A shows sample reservoir 12 is filling with sample air 30 and clean air from source 14' is being injected into plasma 28. FIG. 3B shows valves 15, 16, and 17 being activated simultaneously resulting in the flow of sample air 30 being diverted directly to vacuum pump 26 via valve 16 and bypassing sample reservoir 12. Valves 13 and 14 are not yet activated, and consequently, sample loop reservoir 12 remains isolated from plasma 28 and clean air from source 14' continues to flow to plasma 28. At the instant that valves 15, 16, and 17 are activated, however, valve 18 also is activated, allowing pressurized air at atmospheric pressure from source 19 to enter the upstream end of sample reservoir loop 12 at precisely the same location that carrier air from source 14' will enter later during the loop purging portion of the duty cycle. This pressurized air from source 19 is regulated by a pre-set needle valve 19' for precise control and enters the sample reservoir loop 12 to relieve the residual vacuum created by vacuum pump 26 earlier in the duty cycle. Needle valve 19' is required to limit the flow of pressurized air during the one second interval that valve 18 is open so that pressure in sample reservoir 12 is just equalized to atmospheric pressure and not over-pressurized.

Exactly one second after valves 15, 16, 17, and 18 are activated, valve 18 is deactivated and valves 13 and 14 are activated simultaneously. The flow of equalization air from source 19 stops, sample reservoir loop 12 is no longer isolated from plasma 28. Simultaneously, the flow of clean or "carrier" air from source 14' is diverted to the upstream end of sample reservoir loop 12 to push resident sample air 30 through duct 11 and into plasma 28.

After analysis and measurements are made on the injected sample air 30 in ICP-AES apparatus 25, solenoid valves are deactivated in a reverse sequence allowing the interface to revert back to its loop-filling mode.

As mentioned above, the sequential activation of the valves is controlled by computer software commands, such as those involving the output of direct current control signals from a digital to analog converter installed in the computer. The control signals are used to trigger electronic relays which in turn switch on or off, a suitable power source for the valves, such as a 1 to 10 volt signal for the solenoid actuated, or activated, valves.

Figure 4:
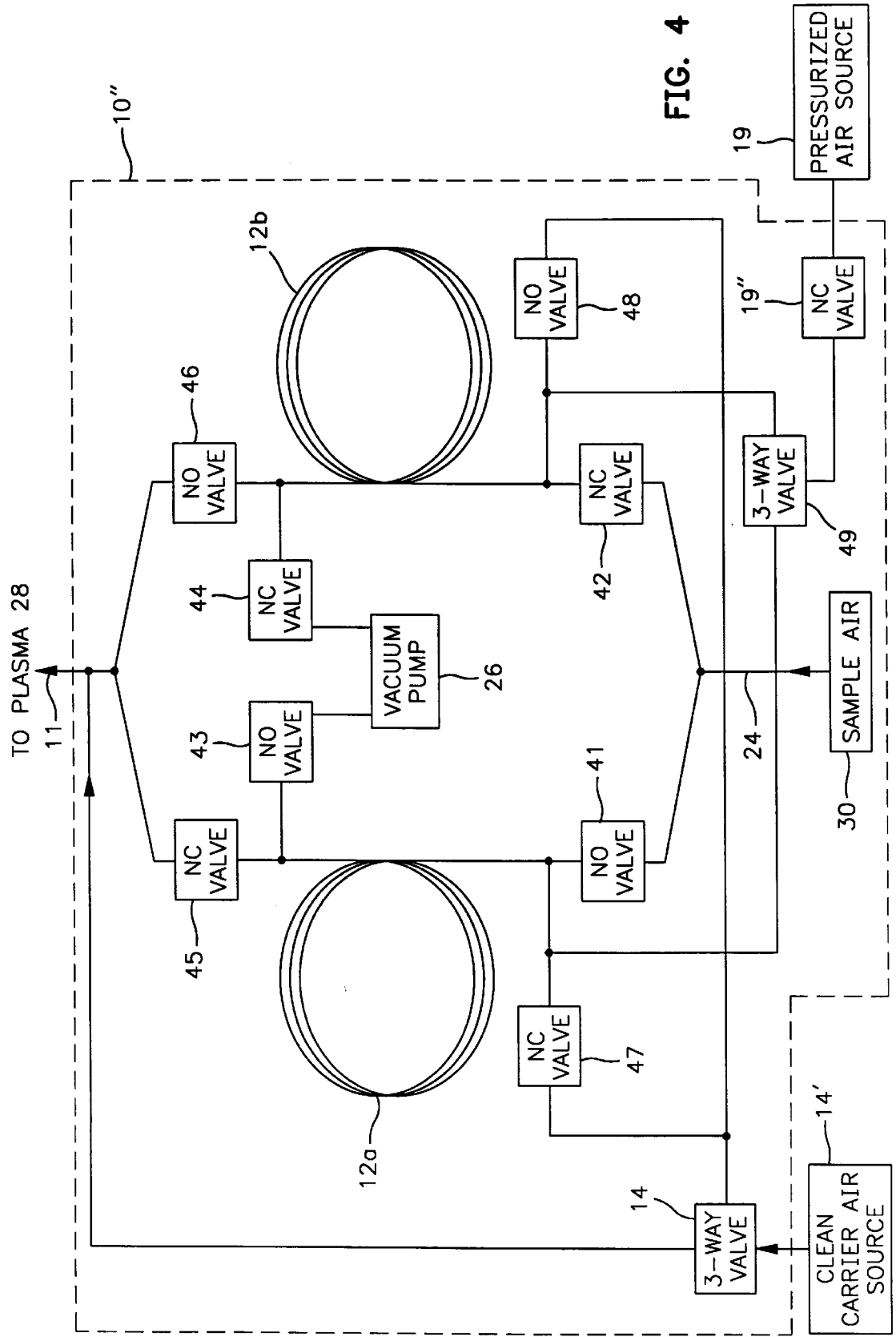
FIG. 4 is another embodiment of this invention having a sampling interface provided with a pair of sampling reservoirs for improved duty cycle operation.

Referring to FIG. 4 of the drawings, another embodiment of sampling interface 10" of this invention is set forth which has two sample reservoir loops 12a and 12b which alternately, or reciprocally, are filled with and purged of alternate aliquots of sample air 30. Typically, the tubing used for the reservoir loops may be about twenty-five feet in length and could have three-eighths inch outer diameters and 0.30 inch inner diameters. Other lengths and sizes may be selected as well as a situation calls for.

This dual reciprocating sample reservoir (loop) design also requires pressure equalization of the sample loops to avoid perturbation of plasma 28 such as occurs with the single loop design described above. While the dual sample loop approach offers certain analytical advantages, the added complexity associated with the extra solenoid activated valves required for operation make the pressure equalization issue more complicated but yet, solvable. The dual sample reservoir design of FIG. 4 has numbered valves marked as normally open NO or normally closed NC as described above.

Sample air 30 is continuously fed under vacuum from isokinetic sampler 23, through line 24, and to sampling interface 10". A first stream of sample air 30 passes through valve 41, traverses left-hand sample reservoir loop 12a and exits through valve 43 to vacuum pump 26. Meanwhile, while the left-hand loop is filling with the first stream, the contents of right-hand sample reservoir loop 12b (a previous stream of sample air 30) are being purged, fed through valve 46 and introduced into plasma 28. Purging is accomplished by the flow of pressurized air from 3-way valve 49 through the upstream end of right-hand sample reservoir loop 12b.

Appropriate synchronized control signals from computer 29 are coupled to isokinetic sampler 23, ICP-AES apparatus 25, pump 26, and sampling interface 10". These signals control the flow of the sample air stream 30 into sampling interface 10" to permit subsequent analysis of gases contained in sample reservoir loops 12a and 12b. The solenoid valves are activated in a precise sequential order as follows. Valves 41, 42, 43, 44, 46, and 49 are simultaneously activated thereby diverting the flow of the next aliquot of sample air 30 to fill right-hand sample reservoir loop 12b and to leave left-hand sample reservoir loop 12a isolated from both vacuum pump 26a and plasma 28. Simultaneously, at the exact instant that valves 41, 42, 43, 44, and 49 are activated, valves 14 and 19" also are activated causing carrier air from source 14' to be diverted directly to plasma 28 through valve 14 and causing pressurized air at atmospheric pressure from source 19 to pass through valve 19" and to be diverted by valve 49 to the upstream end of left-hand sample reservoir loop 12a. This relieves the partial vacuum in loop 12a that is attributed to loop a being connected earlier to vacuum pump 26. Exactly one second after valves 41, 42, 43, 44, 14, 49, and 19" are activated, valve 19" is deactivated, thereby switching off pressurized air from pressurized gas source 19, valve 14 is deactivated, and valves 45 and 47 are activated resulting in the flow of carrier air from 3-way valve 14 to the upstream end of left-hand sample reservoir loop 12a. The aliquot of sample air 30 in left-hand sample reservoir loop 12a, therefore, is forced out of loop 12a, through valve 46, and into plasma 28 at flow rates and pressures which are the same as those coming from source 14'. These are the same flow rates and pressures have been predetermined to be acceptable, or optimum, for analysis processing by ICP-AES apparatus 25.

When measurements on the aliquot of sample air 30 from left-hand sample reservoir loop 12a are complete, computer 29 provides control signals to switch back to right-hand sample reservoir loop 12b. First, valves 41, 42, 43, 44, and 49 are simultaneously deactivated thereby diverting the flow of an aliquot of sample air 30 to fill left-hand sample reservoir loop 12a once again and leaving right-hand sample reservoir loop 12b isolated from both vacuum pump 26 and plasma 28. At the exact instant that valves 41, 42, 43, 44, and 49 are deactivated, valves 14 and 19" also are simultaneously activated causing carrier air from source 14' to be diverted directly to plasma 28 through valve 14, and pressurized air from valve 19" to be diverted by valve 49 to the upstream end the right-hand sample reservoir loop 12b. This relieves the partial vacuum in loop 12b that is attributed to loop 12b's being connected earlier to vacuum pump 26. Exactly one second after valves 41, 42, 43, 44, 14, 49, and 19" are activated, valve 19" is deactivated, thereby switching off pressurized air from source 19, valve 14 is deactivated, and valves 46 and 48 are deactivated resulting in the flow of carrier air from source 14' through 3-way valve 14 to the upstream end of right-hand sample reservoir loop 12b. The aliquot of sample air 30 in right-hand sample reservoir loop 12b, therefore, is pushed out of loop 12b, forced through valve 46, and into plasma 28 at flow rates and pressures that are the same as those coming from source 14'. These are the same flow rates and pressures that have been predetermined to be acceptable, or optimum, for analysis processing by ICP-AES apparatus 25.

The aforestated process for filling, equalizing, and purging alternate streams of sample air 30 in sample reservoir loops 12a and 12b is continued ad infinitum or until meaningful analyses are concluded.

Configured as described herein, sampling interface 10" having dual reciprocating sample reservoirs can theoretically double the measurement frequency relative to a single elongate reservoir loop arrangement. By allowing measurements to be made at more frequent intervals using more representative sampling of extracted flue gases or air, sampling interface 10" with dual reciprocating sample reservoirs may permit the acquisition of hazardous emissions monitoring data that is more meaningful in terms of its temporal characteristics.

The dual sample loop arrangement of sampling interface 10" provides another advantage over the prior art since the time required to achieve introduction of a steady state sample into plasma 28 can be reduced from the present 15–20 second wait to an approximately 5-second wait. This is because since sample introduction will no longer alternate between sample air and clean air in a single loop. Thus, by incorporating the second elongate reservoir or sample loop, wait times, normally required for a single sample reservoir to be recharged, are all but eliminated. Extracted stack air, otherwise exhausted from the system during the time that sample air resident in a single sample reservoir or sample loop arrangement is being purged and introduced into the plasma spectrometer, can now be used to fill or recharge the second elongate reservoir or loop to permit immediate introduction of a fresh aliquot of sample air into the plasma spectrometer once the sample air in the previous loop is depleted. The obvious advantage is that measurements can be made on portions of air that would have been discarded using a single elongate reservoir loop arrangement.

The sampling interfaces described herein do not cause appreciable losses or, settling-out, of particulates in the elongate reservoirs (loops) as the aliquots of sample air pass through them.

The arrangements of valves and ducting of samples of the embodiments disclosed herein are not to be construed as limiting, but rather are intended for the purpose of demonstrating this inventive concept. Therefore, it is to be understood that, having the teachings of this invention in mind, one skilled in the art to which this invention pertains can select other valves and/or arrangements of valves, other combinations of three-way, two-way, check valves, etc. and still be within the scope of this invention. Similarly, the flow rates, pressures, types of gases relied upon, plasma gases, etc. that were disclosed herein were selected for the purpose of demonstration of this invention. They are not intended to limit the applications and scope of this invention.

It should be readily understood that many modifications and variations of the present invention are possible within the purview of the claimed invention. It is therefore to be understood that within the scope of the appended claims the invention may be practiced otherwise than as specifically described.

I claim:

1. A sampling interface comprising:
an elongate reservoir;
first means coupled to said elongate reservoir for switching sample air flowing at a first rate and pressure into said elongate reservoir;
means coupled to said elongate reservoir for coupling a first source of pressurized gas to said elongate reservoir to change pressure therein from said first pressure to a second pressure; and
second means coupled to said elongate reservoir for switching a second source of pressurized gas thereto at said second pressure and a second flow rate different than said first flow rate to force said sample air in said elongate reservoir out of said elongate reservoir at said second flow rate and pressure.

2. A structure according to claim 1 further including:
means coupled to said elongate reservoir for providing said first source of pressurized gas at said second pressure into said elongate reservoir between switching said sample air into and out of said elongate reservoir.

3. A structure according to claim 2 in which said coupling means prevents transmitting suction force to plasma.

4. A structure according to claim 3 further including:
means coupled to said elongate reservoir for drawing a vacuum to suck said sample air into said elongate reservoir at said first flow rate and first pressure when said first switching means is activated.

5. A structure according to claim 4 further including:
means coupled to said elongate reservoir for supplying said second source of pressurized gas to said elongate reservoir at said second flow rate and pressure when said second switching means is activated.

6. A structure according to claim 5 in which said elongate reservoir is an elongate length of tubing arranged in a loop.

7. A structure according to claim 6 in which said first switching means is a pair of valves, one normally open and the other normally closed, mounted at the upstream end of said loop to alternately couple to, or isolate from, a heated sample line carrying the sample air stream to the interface, and a said second switching means is a pair of valves, one normally open and the other normally closed, mounted at the downstream end of said loop to alternately couple to, or isolate said loop from the plasma.

8. A method for interfacing comprising the steps of:
switching sample air flowing at a first rate and pressure into an elongate reservoir;
coupling a first source of pressurized gas to said elongate reservoir to change pressure therein from said first pressure to a second pressure thereby preventing the transmission of suction force to plasma in a plasma torch; and
switching a second source of pressurized gas to said elongate reservoir at said second pressure and a second flow rate different than said first flow rate to force said sample air in said elongate reservoir out of said elongate reservoir at said second flow rate and pressure.

9. A method according to claim 8 further including the step of:
introducing said first source of pressurized gas at said second pressure into said elongate reservoir between switching said sample air into and out of said elongate reservoir.

10. A method according to claim 8 wherein said interfacing is between sample air at a first pressure and flow rate and a plasma torch operating at a second pressure and flow rate.

11. A method according to claim 10 further including the step of:
drawing a vacuum to suck said sample air into said elongate reservoir at said first flow rate and first pressure when said first switching means is activated.

12. A method according to claim 11 further including the step of:
supplying said second source of pressurized gas at said second flow rate and pressure to said elongate reservoir when said second switching means is activated.

13. A method according to claim 12 in which said elongate reservoir is an elongate length of tubing arranged in a loop.

14. A sampling interface comprising:

first and second elongate reservoirs;

first means coupled to a heated sample line for alternately switching streams of sample air flowing at a first rate and pressure into said first and second elongate reservoirs;

means coupled to said first and second elongate reservoirs for alternately coupling a first source of pressurized gas to said first and second elongate reservoirs to alternately change pressure in each from said first pressure to a second pressure; and second means coupled to said first and second reservoirs for alternately switching a second source of pressurized gas thereto at said second pressure and a second flow rate different than said first flow rate to alternately force said aliquots of sample air in said first and second reservoirs out of said first and second reservoirs at said second flow rate and pressure.

15. A structure according to claim 14 further including:

means coupled to said first and second elongate reservoirs for alternately providing said first source of pressurized gas at said second pressure into said elongate reservoir between switching said aliquots of sample air into and out of said first and second elongate reservoirs.

16. A structure according to claim 15 in which said alternately coupling means prevents transmitting suction force to plasma.

17. A structure according to claim 16 further including:

means coupled to said first and second elongate reservoirs for alternately drawing a vacuum to suck said aliquots of sample air into said first and second elongate reservoirs at said first flow rate and first pressure when said first switching means is alternately activated.

18. A structure according to claim 17 further including:

means coupled to said first and second elongate reservoirs for alternately supplying said second source of pressurized gas to said first and second elongate reservoirs at said second flow rate and pressure when said second switching means is alternately activated.

19. A structure according to claim 18 in which said first and second elongate reservoirs are two elongate lengths of tubing arranged in two loops.

20. A structure according to claim 19 in which said first switching means is a pair of valves, one normally open and the other normally closed, mounted at the upstream end of said loop to alternately couple to, or isolate from, a heated sample line carrying the sample air stream to the interface and extending from an isokinetic sampler and a said second switching means is a pair of valves, one normally open and the other normally closed, mounted at the downstream end of said loop to alternately couple to, or isolate said loop from the plasma.

21. A method for interfacing comprising the steps of:

alternately switching aliquots of sample air flowing at a first rate and pressure into first and second elongate reservoirs;

alternately coupling a first source of pressurized gas to said first and second elongate reservoirs to alternately change pressure therein from said first pressure to a second pressure thereby preventing the transmission of suction force to plasma in a plasma torch; and alternately switching a second source of pressurized gas to said first and second elongate reservoirs at said second pressure and a second flow rate different than said first flow rate to alternately force said aliquots of sample air in said first and second elongate reservoirs out of said first and second elongate reservoirs at said second flow rate and pressure.

22. A method according to claim 21 further including the step of:

alternately introducing said first source of pressurized gas at said second pressure into said first and second elongate reservoirs between switching said aliquots of sample air into and out of said first and second elongate reservoirs.

23. A method according to claim 22 wherein said interfacing is between aliquots of sample air at a first pressure and flow rate and a plasma torch operating at a second pressure and flow rate.

24. A method according to claim 23 further including the step of:

alternately drawing a vacuum in said first and second elongate reservoirs to alternately suck said aliquots of sample air into said first and second elongate reservoirs at said first flow rate and first pressure when said first switching means is alternately activated.

25. A method according to claim 24 further including the step of:

alternately supplying said second source of pressurized gas at said second flow rate and pressure to said first and second elongate reservoirs when said second switching means is alternately activated.

26. A method according to claim 25 in which said first and second elongate reservoirs are two elongate lengths of tubing arranged in two loops.

27. A sampling interface comprising:

an elongate reservoir;

at least one inlet valve coupled to said elongate reservoir to switch sample air flowing at a first rate and pressure into said elongate reservoir;

at least one coupling valve connected to said elongate reservoir to couple a first source of pressurized gas to said elongate reservoir to change pressure therein from said first pressure to a second pressure; and at least one outlet valve coupled to said elongate reservoir to switch a second source of pressurized gas thereto at said second pressure and a second flow rate different than said first flow rate to force said sample air in said elongate reservoir out of said elongate reservoir at said second flow rate and pressure.

28. A structure according to claim 27 in which said coupling valve prevents transmitting suction force to plasma.

29. A sampling interface comprising:

first and second elongate reservoirs;

at least one inlet valve coupled to said elongate reservoir to alternately switch aliquots of sample air flowing at a first rate and pressure into said first and second elongate reservoirs;

at least one coupling valve connected to said first and second elongate reservoirs to alternately couple a first source of pressurized gas to said first and second elongate reservoirs to alternately change pressure in each from said first pressure to a second pressure; and at least one outlet valve coupled to said first and second reservoirs to alternately switch a second source of pressurized gas thereto at said second pressure and a second flow rate different than said first flow rate to alternately force said aliquots of sample air in said first and second reservoirs out of said first and second reservoirs at said second flow rate and pressure.

30. A structure according to claim 29 in which said alternately coupling valve prevents transmitting suction force to plasma.

* * * * *